United States Patent
Ho et al.

(10) Patent No.: US 8,852,576 B2
(45) Date of Patent: Oct. 7, 2014

(54) MODIFIED SODIUM IODIDE SYMPORTER PROTEINS AND USES THEREOF

(75) Inventors: Tin-Yun Ho, Taichung (TW); Chien-Yun Hsiang, Taichung (TW); Shih-Lu Wu, Taichung (TW); Ji-An Liang, Taichung (TW); Chia-Cheng Li, Taichung (TW); Hsin-Yi Lo, Taichung (TW)

(73) Assignee: China Medical University, Taichung (TW)

( * ) Notice: Subject to any disclaimer, the term of this patent is extended or adjusted under 35 U.S.C. 154(b) by 358 days.

(21) Appl. No.: 12/901,096

(22) Filed: Oct. 8, 2010

(65) Prior Publication Data

US 2012/0027676 A1    Feb. 2, 2012

(30) Foreign Application Priority Data

Jul. 28, 2010 (TW) .............................. 99124881 A

(51) Int. Cl.
| | |
|---|---|
| A01N 63/00 | (2006.01) |
| A61K 48/00 | (2006.01) |
| C12N 5/00 | (2006.01) |
| C12N 15/00 | (2006.01) |
| C07K 14/705 | (2006.01) |

(52) U.S. Cl.
CPC .................................. C07K 14/705 (2013.01)
USPC ..................... 424/93.21; 424/93.7; 514/44 R; 435/325; 435/320.1

(58) Field of Classification Search
None
See application file for complete search history.

(56) References Cited

U.S. PATENT DOCUMENTS

2006/0004191 A1    1/2006    Jhiang et al.

FOREIGN PATENT DOCUMENTS

| WO | 97/28175 | 8/1997 |
|---|---|---|
| WO | 2004/000236 | * 12/2003 |

OTHER PUBLICATIONS

Phillips, A., J Pharm Pharmacology 53: 1169-1174.*
Shen et al. 2001. Thyroid 11:415-425.*
Prockop et al. 2007. Blood 109:3147-3151.*
Kunkel, T., "Rapid and efficient site-specific mutagenesis without phenotypic selection," Proc. Natl. Acad. Science, vol. 82, 1985 Genetics, pp. 488-492.
European Search Report dated Jul. 11, 2011 of Application No. 10190494.4.
Wu et al., "Histidine residue at position 226 is critical for iodide uptake activity of human sodium/iodide symporter," Journal of Endocrinology, 2008, pp. 213-219, vol. 199.
De La Vieja et al., "Amino Acid Residues in Transmembrane Segment IX of the Na+/I– Symporter Play a Role in Its Na+ Dependence and Are Critical for Transport Activity," Journal of Biological Chemistry, Aug. 31, 2007, vol. 282—No. 35.

* cited by examiner

*Primary Examiner* — Shulamith H Shafer
(74) *Attorney, Agent, or Firm* — Ping Wang; Andrews Kurth LLP

(57) ABSTRACT

A modified sodium iodide symporter (NIS) protein is provided. The modified NIS protein comprises an amino acid sequence of SEQ ID NO.1 with the proviso that at least one amino acid residue within SEQ ID NO. 1 is changed. The modified NIS protein has an enhanced transport function, and the expression of the modified NIS protein in the cells results in higher intracellular levels of a substrate of a NIS protein than does the expression of the same amount of a wild-type NIS protein.

5 Claims, 1 Drawing Sheet
(1 of 1 Drawing Sheet(s) Filed in Color)

MODIFIED SODIUM IODIDE SYMPORTER PROTEINS AND USES THEREOF

CROSS-REFERENCES TO RELATED APPLICATIONS

This application claims priority to Taiwan Patent Application No. 099124881 filed on Jul. 28, 2010.

BACKGROUND OF THE INVENTION

1. Field of the Invention

The present invention relates to a modified sodium iodide symporter protein and its uses, and particularly relates to the uses of the modified sodium iodide symporter protein for increasing the substrates of the sodium iodide symporter protein within cells in vitro or in vivo.

2. Descriptions of the Related Art

The main function of thyroid hormones in the human body is to regulate physiological functions and promote metabolism. For example, thyroid hormones can regulate the oxygen consumption of cells, respiratory rate, body temperature, heartbeat, blood flow, etc., and also can promote the metabolism of fats, proteins, and carbohydrates. Iodine (I) is an essential element in thyroid hormones. Thyroid hormones are produced by the thyroid gland, and via a sodium iodide symporter (NIS) protein on the cell membrane of the thyroid gland, iodide ions (I$^-$) in the blood are transferred to thyroid cells by active transport to synthesize thyroid hormones.

Thyroid cancer is a malignant neoplasm that commonly occurs in the region of the neck. Thyroid cancer has a long latency period with a fast transfer rate and has become one of the leading cancers for the female population in Taiwan over recent years. Radioactive iodine therapy is commonly used for the treatment of thyroid cancer. The specificity of the NIS protein transporting iodide ions is applied in this therapy to transfer a radioactive I-131 isotope into thyroid cancer cells to achieve the efficacy of killing cancer cells. Thus, in radioactive iodine therapy, the function of the NIS protein to transport iodide ions into the thyroid cancer patient has become a key factor in treatment. If the NIS protein cannot promptly transfer a sufficient concentration of radioactive iodide ions into thyroid cancer cells, then the cancer cells cannot be effectively killed to promote cancer therapy.

US Laid-Open Patent Application No. 2006/0004191 A1 discloses a modified NIS protein, of which the transport function for I$^-$ ions is enhanced by increasing the number of positive charges of the wild-type NIS proteins. Although this patent application mentions that a substitution method (i.e., neutral uncharged or negatively charged amino acids in the wild-type NIS protein are substituted by positively charged amino acids) or an addition method (i.e., positively charged amino acids are added to the wild-type NIS protein) can be used to modify the NIS protein and increase the amount of positive charged amino acids in the wild-type NIS protein, according to the examples disclosed therein, ten positively charged amino acids are added to the wild-type NIS protein to enhance its transport capability.

In fact, it is not that straightforward to simply replace the neutral uncharged or negatively charged amino acids with the positively charged amino acids within the NIS protein to achieve the improvement result as claimed in US 2006/0004191 A1. Furthermore, based on the teaching of US 2006/0004191 A1, if multiple positively charged amino acids are intentionally added to the wild-type NIS protein to increase the number of positively charged amino acids, then a sufficient amount of positively charged amino acids are required to achieve such an improved effect, thus increasing the cost of NIS protein production. As a result, an accurate and efficient modification method is still needed to increase the transport function of the NIS protein.

The research result of the present invention was carried out based on the above demand, and the inventors of the present invention found that the ability to transfer iodide ions of the NIS protein can be greatly enhanced by modifying a single or more amino acid residues within the NIS protein.

SUMMARY OF THE INVENTION

One objective of this invention is to provide a modified sodium iodide symporter (NIS) protein, comprising an amino acid sequence of SEQ ID NO.1 with the proviso that at least one amino acid residue within SEQ ID NO. 1 is changed.

Another objective of this invention is to provide a polynucleotide encoding the modified NIS protein described above and an expression vector comprising the polynucleotide.

Still another objective of this invention is to provide a method for increasing the substrate of the NIS protein within a cell in vitro, comprising the following steps:

a) introducing the modified NIS protein into a cell in vitro; and b) putting the cell into contact with one or more substrates of the NIS protein.

Yet a further objective of the present invention is to provide a method for increasing the substrate of the NIS protein within a cell in vivo, comprising the following steps:

I) introducing the modified NIS protein into a cell in vitro;

II) transplanting the cell into an animal body; and

III) allowing the cell in the animal body to be contacted with one or more substrates of the NIS protein.

The detailed technology and preferred embodiments implemented for the present invention are described in the following paragraphs for people skilled in this field to well appreciate the features of the claimed invention.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DESCRIPTION OF THE PREFERRED EMBODIMENT

Figure 1:
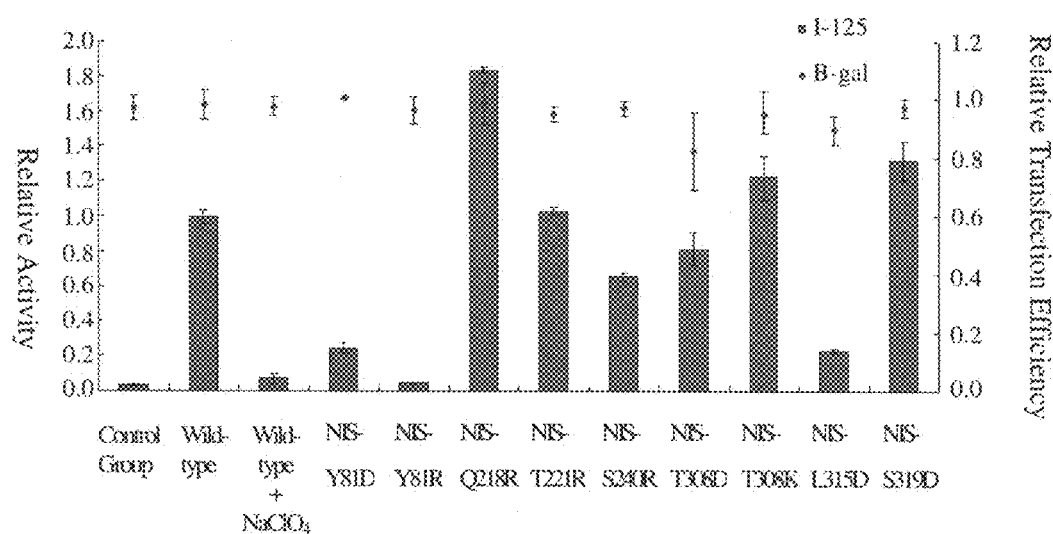
FIG. 1 is a statistic bar diagram illustrating the iodine transport function of the wide-type sodium iodide symporter protein (NIS-wt) or the mutant NIS proteins.

Unless there is an explanation in this article otherwise, the words "a", "an", "the", and other analogous words in this specification (especially in the following claims) should be considered as a singular or plural form.

As described above, in clinical medicine, radioactive iodine therapy has been used for thyroid cancer therapy, wherein thyroid cancer cells are killed via the characteristic of the sodium iodide symporter (NIS) protein specifically transporting radioactive I$^-$ ions. Because radioactive iodine therapy has high specificity to thyroid cancer cells, it becomes one of the effective methods for thyroid cancer therapy. However, this method depends on the transport ability of the NIS protein within the thyroid cancer patients themselves. If the NIS protein cannot effectively transport I⁻ ions, then the treatment effect will be limited. Even though there is literature suggesting a method for modifying the NIS protein to increase its transport ability, the method still cannot improve the NIS protein accurately and effectively.

The NIS protein is an intrinsic membrane protein consisting of about 650 amino acids (the amino acid sequence is shown in SEQ ID NO.1). The protein has thirteen transmembrane domains and can act as an ion pump to simultaneously transport one iodide (I⁻) ion with two sodium (Na⁺) ions into the thyroid gland cells. The inventors of the present invention found that the transport function of the NIS protein can be enhanced by modifying amino acids in the NIS protein.

The present invention provides a modified NIS protein with an enhanced transport function. The NIS protein of the present invention is made by changing at least one amino acid residue within the amino acid sequence (SEQ ID NO.1) of the wild-type NIS protein to increase the transport function for substrates thereof, and therefore it can be used to increase the amount of substrates of the NIS protein in cells (i.e., the expression of the NIS protein of the present invention in cells results in higher intracellular levels of substrates of the NIS protein than does the expression of the same amount of the wild-type NIS protein).

According to the present invention, the modification to the NIS protein comprises the replacement of a positively charged or a neutral, uncharged amino acid residue in the protein with a negatively charged amino acid residue to increase the number of negative charges in the NIS protein to enhance its transport ability. For example, aspartic acid (negatively charged) can be used to replace the residue serine (neutral, uncharged) 319 in the NIS protein. Therefore, in the present invention, the modified NIS protein can comprise an amino acid sequence of SEQ ID NO.1, and at least one amino acid residue within the amino acid sequence is changed to a negatively charged amino acid.

According to the present invention, the modification to the NIS protein may also comprise the replacement of a negatively charged or neutral uncharged amino acid residue in the protein with a positively charged amino acid residue to increase the amount of positive charges in the NIS protein to enhance its transport function. For example, the residue glutamine (neutral, uncharged) 218 can be replaced by arginine (positively charged), or, the residue threonine (neutral, uncharged) 308 can be replaced by lysine (positively charged). In one embodiment of the present invention, the residue glutamine 218 of the NIS protein is replaced by arginine.

Preferably, the NIS protein of the present invention comprises the amino acid sequence of SEQ ID NO.1 with the proviso that at least one of the following conditions is satisfied: (1) residue glutamine (Q) 218 is replaced by arginine (R); (2) residue threonine (T) 308 is replaced by lysine (K); and (3) residue serine (S) 319 is replaced by aspartic acid (D). Not limited by theory, the inventors of the present invention believe that by modifying any one of the above three amino acid residues, the 3D structure of the NIS protein on the cell membrane can be changed, and the transport function thereof can be enhanced accordingly.

In one embodiment of the present invention, the residue glutamine 218 is replaced by arginine (abbreviated as "NIS-Q218R" in the following paragraphs), the residue threonine 308 is replaced by lysine (abbreviated as "NIS-T308K" in the following paragraphs), and/or the residue serine 319 is replaced by aspartic acid (abbreviated as "NIS-S319D" in the following paragraphs) in the NIS protein by site-directed mutagenesis to greatly enhance its transport function. In terms of the structure of the NIS protein within a cell, all the above three amino acid residues present at the extracellular location on the cell membrane. As illustrated in the following examples, the transport ability of the NIS protein of the present invention can be improved by about 200% when compared to the wild-type NIS protein (abbreviated as "NIS-wt" in the following paragraphs).

The NIS protein can be modified with any suitable approaches to provide the modified NIS protein of the present invention. For example, the NIS protein of the present invention can be synthesized by an amino acid synthesizer, wherein it only carries out the replacement when the synthesis of the amino acid residues 218, 308, and/or 319 proceeds. Alternatively, through molecular biotechnology, a set of primers for site-directed mutagenesis can be designed, and the nucleic acids of the amino acid residues 218, 308, and/or 319 can be modified by referring to the codon table, and then expression is carried out in a host cell to obtain the NIS protein of the present invention.

It is well known that the NIS protein, apart from transporting Na⁺ and I⁻ ions out of cells, can also transfer other substrates, such as pertechnate ion (TcO₄⁻), perrhenate ion (ReO₄⁻), astatide ion (At⁻), etc. Therefore, the NIS protein of the present invention has enhanced transport function for substrates selected from a group consisting of the following ions: Na⁺, I⁻, TcO₄⁻, ReO₄⁻, At⁻, and combinations thereof. Preferably, the NIS protein has an enhanced transport function for I⁻ ions.

As described above, the radioactive iodine therapy is based on the ability for the NIS protein transporting radioactive I⁻ ions to kill thyroid cancer cells then further treat thyroid cancers. Due to the enhanced transport function for ions of the NIS protein of the present invention, when the protein is applied to the transferring of radioactive I⁻ ions, the treatment effect of iodide ions on thyroid cancer can be improved. In addition, the NIS protein, apart from existing in the thyroid gland, can also exists in other tissues (such as nasal mucosa, stomach, salivary gland, etc), but the amount of the NIS protein existing in non-thyroid gland tissue is relatively low. Therefore, when cancer cells appear in other tissues containing the NIS protein within the body, the enhanced transport function of the NIS protein of the present invention can be used to treat the relevant tissue but not be limited to the thyroid gland tissue.

Radioactive I⁻ ions not only can be applied to cancer therapy, but also can be applied to molecular imaging. Based on the radioactivity of radioactive I⁻ ions, a single photon emission computed tomography (SPECT) or Gamma-ray scanner can be used to detect or trace the activity and state of the radioactive I⁻ ions in the body to achieve the effect of real-time detection for cancer therapy. Because the NIS protein of the present invention can effectively transfer radioactive I⁻ ions into cancer cells, the process in which radioactive I⁻ ions kill cancer cells can be fully monitored. Therefore, the NIS protein of the present invention is especially advantageous when applied to molecular imaging.

The present invention also provides a polynucleotide encoding the NIS protein of the present invention and the polynucleotide comprises a nucleic acid sequence of SEQ ID NO.2, SEQ ID NO.3, SEQ ID NO.4, SEQ ID NO.5, SEQ ID NO.6, SEQ ID NO.7, or SEQ ID NO.8. Preferably, the polynucleotide comprises a nucleic acid sequence of SEQ ID NO.2.

The present invention also provides an expression vector comprising the above polynucleotide. When the expression vector is used to carry out expression within a host cell, the NIS protein of the present invention can be generated. Therefore, the expression vector can be applied in cancer therapy, molecular imaging, or a combination thereof. These applications are described above.

Any known or commercial vector can be used to construct the expression vector of the present invention, as long as it is replicable and can function within a host cell. For example, when the prokaryotes are used as a host cell, vectors such as pBluescript® II KS (+/−) phagemid vector or pUC18 from Stratagene LTD, U.S. can be used. When the eukaryotes are used as the host cell, vectors such as pcDNA3.1, pSV40/neo, or a viral vector can be used.

Because the modified NIS protein of the present invention has enhanced transport function, it can be used to increase the amount of substrates of the NIS protein in cells. Therefore, the present invention further provides a method for increasing the amount of substrates of the NIS protein in cells in vitro or in vivo.

The method for increasing the amount of substrates of the NIS protein in cells in vitro of the present invention comprises the following steps: a) introducing the NIS protein of the present invention into a cell in vitro; and b) putting the cell in contact with one or more substrates of the NIS protein. The method for increasing substrates of the NIS protein in cells in vivo comprises the following steps: I) introducing the NIS protein of the present invention into a cell in vitro; II) transplanting the cell into an animal body; and III) putting the cell in contact within the animal body with one or more substrates of the NIS protein.

The method of the present invention can increase the amount of substrates of the NIS protein within cells. The substrates can be, for instance, $Na^+$, $I^-$, $TcO_4^-$, $ReO_4^-$, or $At^-$ ions. Preferably, the method can be used to increase the amount of $I^-$ ions within cells.

In step a) or step I) of the above method of the present invention, the NIS protein of the present invention can be introduced into a cell in vitro with any suitable approach. For example, but not limited thereby, it can be carried out through the following steps: a1) introducing an expression vector comprising a polynucleotide encoding the NIS protein of the present invention (i.e. the express vector of the present invention) into the cell in vitro; and a2) culturing the cell to express the NIS protein.

In step a1), the expression vector can be introduced into a cell by known transfection methods. For example, a PEG protoplast method, chemical method, electroporation, gene gun transfection, etc, can be used. In one embodiment, electroporation is used for transformation. In this process, as a cell is stimulated with an electric current, the permeability of the cell membrane would suddenly increase, and allow a heterologous gene (for example, an expression vector) to enter the cell. The electroporation is advantageous because it is easy and simple in terms of operation, and is suitable for various types of cells and the success rate of transformation is high.

In step a1), the polynucleotide comprises a nucleic acid sequence of SEQ ID NO.2, SEQ ID NO.3, SEQ ID NO.4, SEQ ID NO.5, SEQ ID NO.6, SEQ ID NO.7, or SEQ ID NO.8. Preferably, the polynucleotide comprises a nucleic acid sequence of SEQ ID NO.2.

In step a2), the cell is cultured to express the NIS protein of the present invention. Then, the NIS protein will be transported to the cell membrane via cellular physiological mechanism to carry out its transport function. Then, the NIS protein of the present invention is introduced into the cell.

After the NIS protein of the present invention is introduced into the cell in vitro, step (b) can be carried out to put the cell in contact with one or more substrates of the NIS protein. Alternatively, if the intention is to increase the substrates of the NIS protein in cells in vivo, then step II) can be carried out first to transplant the cell into an animal body, and step III) is then carried out, allowing the cell within the animal body to get in contact with one or more substrates of the NIS protein. In step II), any suitable method can be used to transplant the cell into the animal body. For example, intraperitoneal injection, intravenous injection, etc., can be used for cell inoculation.

In step (b) or step III), any suitable method can be used to make the cell get in contact with the substrate. For example, the substrate can be simply added to the medium containing the cell, or the cell-transplanted animal can take the substrate to make the cell get in contact with the substrate. Because there are NIS proteins with enhanced transport function on the cell membrane of the cell, the substrate can be easily transferred into the cell to increase the amount of the substrate in the cell.

Because the method of present invention can increase the amount of ions within cells in vitro or in vivo, it can be applied to in vitro or in vivo molecular imagining. For example, the method of the present invention can be applied to in vitro or in vivo cell or tissue testing. By using radioactive $I^-$ ions and a single photon emission computed tomography (SPECT) or γ-radiation scanner to detect or trace the activity and state of the radioactive ions in the cell or tissue, in vitro or in vivo molecular imaging can be carried out.

Hereinafter, the present invention will be further illustrated with reference to the following examples. However, these examples are only provided for illustration purposes, and are not to limit the scope of the present invention.

Example 1

Preparation of Mutant-Type Sodium Iodide Symporter (NIS) Protein

Experiment A. Preparation of Single Strand Phagemid DNA

E. coli (CJ236, purchased from New England BioLabs Ltd, USA) containing the plasmid, pBluescript®II KS(+)-5' hNIS (the polynucleotide of the wild-type sodium iodide symporter protein (NIS-wt)) was placed into the medium (each liter contains 10 g of Tryptone, 5 g of yeast extract, and 10 g of sodium chloride) that contained 15 μg/mL of chloramphenicol, and was shake-cultured in an incubator at 37° C. The next day, the broth was added to the 2xYT medium (each liter contained 16 g of Tryptone, 10 g of yeast extract, and 5 g of sodium chloride) that contained 50 μg/mL of ampicillin (Sigma-Aldrich, USA) and 15 μg/mL of chloramphenicol. The bacteria were shake-cultured in the incubator at 37° C. until the $O.D._{600}$ value of the broth reached 0.3. Then, M13KO7 Helper Phage (purchased from New England BioLabs Ltd, USA) was added to the broth and shake-cultured in the incubator at 37° C. for 1 hour, and 70 μg/mL of kanamycin was then added to the broth and shake-cultured in the incubator at 37° C. for 6 hours. The broth was placed into a centrifuge tube and centrifuged at 12,000 rpm for 15 minutes. The supernatant was collected and placed into another centrifuge tube and centrifuged again. The supernatant was collected and 10 U/μL of DNase I (Deoxyribonuclease I) and 10 μg/mL of RNase A were added. The mixture was reacted at 37° C. for 15 minutes, and ¼ volume of a phage precipitation solution (20% PEG-8000, 3.75 M ammonium acetate) was then added to the mixture. The mixture was placed on ice for 30 minutes and centrifuged at 16,000 rpm for 15 minutes.

After centrifugation, the supernatant was removed, and a Tris buffer was used to dissolve the precipitate. The precipitate was then extracted several times by phenol/chloroform.

The supernatant was collected, and the single strand phagemid DNA was precipitated by alcohol precipitation. Finally, the single strand phagemid DNA was dissolved with water.

Experiment B. Site-Directed Mutagenesis

The neutral (uncharged) and not highly conserved amino acids that were located outside the cell membrane in the NIS protein were selected to prepare mutant NIS proteins by site-directed mutagenesis based on the conformation and the important functional sites of amino acids of the NIS protein.

First, the single strand phagemid DNA (1 µL) that was prepared in Experiment A, a primer comprising the nucleic acid sequence of SEQ ID NO.9 (1.25 µL), a 10-fold annealing buffer solution (1 µL, including 500 mM NaCl, 200 mM Tris-HCl (pH8.0), and 20 mM $MgCl_2$) were added into secondary deionized water (6.75 µL), and were mixed in a test tube. Mineral oil was then added to avoid water evaporation. The mixture was heated in water at 99° C. for 5 minutes, and then gradually cooled to 30° C. with the rate of 1° C. per minute to allow the single strand phagemid DNA and the primer to anneal, and then the mixture was cooled on ice.

Then, a synthetic buffer solution, T4 DNA ligase, T4 DNA polymerase, and T4 gene 32 protein (purchased from Invitrogen Ltd, USA) were added to the test tube, and the tube was placed on ice for 5 minutes, and then the mixture was reacted at 25° C. for 5 minutes, and finally reacted at 37° C. for 90 minutes to carry out PCR. After the reaction was completed, the resultant product was extracted with phenol/chloroform for several times, and then the DNAs were precipitated by alcohol. The precipitated DNAs were dissolved by water and transformed into *E. coli* NM522 (purchased from Stratagene Ltd) by the electroporation method. The broth of *E. coli* NM522 was coated on a culture plate containing ampicillin and incubated in an incubator at 37° C. for 16 to 24 hours. Screening was carried out to obtain *E. coli* NM522 comprising the plasmid DNA containing the polynucleotide of the mutant NIS protein, NIS-Y81D (i.e., the residue tyrosine (Y) 81 in the NIS protein was substituted as aspartic acid (D)).

A single colony of *E. coli* NM522 was selected and placed in the LB medium (each liter contained 10 g of tryptone, 5 g of yeast extract, and 10 g of sodium chloride) containing 50 µg/mL ampicillin and shake-cultured in an incubator at 37° C. for 24 hours. The plasmid DNA of the bacterium was extracted and cut by a restriction enzyme, and the result of site-directed mutagenesis was confirmed by DNA sequencing. The above experimental method was referred to Kunkel, 1985, Rapid and efficient site-specific mutagenesis without phenotypic selection, *Proc. Natl. Acad. Sci. USA*, 82: 488-492, which is incorporated hereinto by reference.

The above procedure was repeated, wherein a primer comprising the nucleic acid sequence of SEQ ID NO. 10, SEQ ID NO.11, SEQ ID NO.12, SEQ ID NO. 13, SEQ ID NO. 14, SEQ ID NO. 16, or SEQ ID NO. 17 was used to make *E. coli* NM522 comprising a plasmid DNA containing the polynucleotide of a mutant NIS protein of NIS-Y81R, NIS-Q218R, NIS-T221R, NIS-S240R, NIS-T308D, NIS-T308K, NIS-L315D, or NIS-S319D. The primer sequences used for the site-directed mutagenesis in the experiment are shown in Table 1.

TABLE 1

| Mutant-type | Primers for site-directed mutagenesis | Sequence |
| --- | --- | --- |
| NIS-Y81D | 5'-CCGTCGGAGGCCGATCGCTATGGCCTCAAGTTCC-3' | SEQ ID NO: 9 |
| NIS-Y81R | 5'-GTCGGAGGCCCGCCGCTATGGCCTCAAGTTCC-3' | SEQ ID NO: 10 |
| NIS-Y81R | 5'-GTCGGAGGCCCGCCGCTATGGCCTCAAGTTCC-3' | SEQ ID NO: 10 |
| NIS-Q218R | 5'-GGGCCCCGACGCGTGCTCACGCTGGCC-3' | SEQ ID NO: 11 |
| NIS-T221R | 5'-GTGCTCAGGCTAGCCCAGAACCACTCCCGG-3' | SEQ ID NO: 12 |
| NIS-S240R | 5'-GACCCGAGGCGCCGCTATACATTCTGG-3' | SEQ ID NO: 13 |
| NIS-T308D | 5'-GTCATGTTTGTCTTCTACGATGACTGCGACCCTC-3' | SEQ ID NO: 14 |
| NIS-T308K | 5'-GTCATGTTTGTCTTCTACAAGGACTGCGACCCTC-3' | SEQ ID NO: 15 |
| NIS-L315D | 5'-GCGACCCTCTTCTCGATGGGCGCATCTCTGCC-3' | SEQ ID NO: 16 |
| NIS-S319D | 5'-CTGGGGCGCATCGATGCCCCAGACCAGTAC-3' | SEQ ID NO: 17 |

Example 2

Iodine Transport Test

SuperFect (purchased from QIAGEN Ltd.) was used to transfer the plasmid DNA containing the polynucleotide of the mutant NIS protein, NIS-Y81D, obtained from Example 1 into the human liver cancer cell line, HepG2, (purchased from ATCC) to allow the expression of the mutant NIS protein. After 24 hours, 1 mL of DMEM (Dulbecco's Modified Eagle Medium) containing 10.2 µCi (micro curie)/mL of iodine-125 (I-125) was added to the cell medium. After being cultured in an incubator at 37° C. for an hour, the cells were collected, and a Cobra II auto-gamma counter (Packard Bio-Science, Dreieich, Germany) was used to measure the radioactivity of I-125 to determine the ability of the NIS protein to transport iodine.

The above procedure was repeated, wherein a plasmid DNA containing the polynucleotide of the mutant NIS protein NIS-Y81R, NIS-Q218R, NIS-T221R, NIS-S240R, NIS-T308D, NIS-T308K, NIS-L315D, or NIS-S319D prepared in Example 1 was used in this experiment. The results are shown in FIG. 1 and Table 2.

TABLE 2

| Group | Relative Activity |
| --- | --- |
| Control group (no I-125 was added) | 0.03 ± 0.003 |
| NIS-wt | 1 |

TABLE 2-continued

| Group | Relative Activity |
|---|---|
| NIS-wt + NaClO$_4$ | 0.07 ± 0.002 |
| NIS-Y81D | 0.24 ± 0.028 |
| NIS-Y81R | 0.04 ± 0.004 |
| NIS-Q218R | 1.83 ± 0.016* |
| NIS-T221R | 1.03 ± 0.022 |
| NIS-S240R | 0.65 ± 0.023 |
| NIS-T308D | 0.81 ± 0.093 |
| NIS-T308K | 1.22 ± 0.473 |
| NIS-L315D | 0.23 ± 0.013 |
| NIS-S319D | 1.26 ± 0.102 |

*For P < 0.05, it showed significant difference when compared to the wild-type NIS protein.

As can be seen from FIG. 1 and Table 2, when compared to the wide-type NIS protein, the mutant-type NIS protein of NIS-Q218R, NIS-T308K, and NIS-S319D showed significant better ability for transporting I$^-$ ions. NIS-Q218R has the best transport ability. Therefore, the present test indicated that the NIS protein obtained by modifying the extracellular amino acids of the wild-type NIS protein has enhanced transport function.

The test also revealed that it is not that simple to change neutral, or negatively charged amino acids in the wild-type NIS protein with positively charged amino acids to improve the transport function of the NIS protein (for example, as shown in the test results of NIS-Y81R, NIS-T221R and NIS-S240R), but the replacement must be implemented on a specific location of the amino acid sequence of the NIS protein for the effect of elevating transport function of the NIS protein to be attained accordingly. On the other hand, the test result of NIS-S319D showed that by replacing neutral (uncharged) amino acids with negatively charged amino acids (i.e., to increase the number of negative charges of the NIS protein), the transport function of the NIS protein can also be improved.

Example 3

Kinetic Test of Iodine Transport

Superfect was used to transfer the plasmid DNA containing the polynucleotide of the mutant-type NIS protein (NIS-Q218R, NIS-T308K, or NIS-S319D) into the human liver cancer cell line, HepG2 to carry out the expression of the protein. After 24 hours, the cells were placed into the medium comprising 6.25 μM (contained 0.390625 μCi/mL I-125), 12.5 μM (contained 0.78125 μCi/mL I-125), 25 μM (contained 1.5625 μCi/mL I-125), 50 μM (contained 3.125 μCi/mL I-125), 100 μM (contained 6.25 μCi/mL I-125), 200 μM (contained 12.5 μCi/mL I-125), 400 μM (contained 25 μCi/mL I-125), 800 μM (contained 50 μCi/mL I-125), or 1600 μM (contained 100 μCi/mL I-125) of sodium iodide. After being cultured for 4 minutes, HepG2 cells were collected, and a Cobra II auto-gamma counter was used to measure the radioactivity of 1-125. The obtained values were inputted into the following equation, and $V_{max}$ and $K_m$ values were calculated by the Lineweaver-Burk plot:

$$v = V_{max} \times [I]/(K_m + [I]) + 0.0156 \times [1] + 2.4588$$

The value (0.0156×[I]+2.4588) from HepG2 cells that comprised the wide-type NIS protein with no addition of sodium iodide was used as a background value. The results are shown in Table 3.

TABLE 3

|  | $V_{max}$ Maximum Velocity | $K_m$ Micromolar concentration |
|---|---|---|
| NIS-wt | 0.55 ± 0.08 | 18.15 ± 3.37 |
| NIS-Q218R | 0.92 ± 0.18 | 58.27 ± 27.93 |
| NIS-T308K | 0.81 ± 0.12 | 55.36 ± 13.61 |
| NIS-S319D | 0.73 ± 0.07 | 94.25 ± 31.12 |

Table 3 showed that compared to the $V_{max}$ value of the wild-type NIS protein, those of the mutant-type NIS proteins of NIS-Q218R, NIS-T308K, and NIS-S319D were obviously higher, indicating that the mutant-type NIS proteins have better ability to transport I$^-$ ions. Besides, NIS-Q218R showed the best transport ability. Therefore, this test illustrated that the NIS protein of the present invention indeed has enhanced transport function. NIS-Q218R was used for the following test.

Example 4

Animal Test—In Vivo Ion Transport Test

SuperFect was used to transfer the plasmid DNA containing the polynucleotide of the mutant-type NIS protein, NIS-Q218R, or the wild-type NIS protein, NIS-wt, into the human liver cancer cell line, HepG2, for the expression of the proteins. After 24 hours, the cells (8.4×10$^4$ cells) were injected to the abdominal cavity of a Balb/c mouse (purchased from National Laboratory Animal Center) by intraperitoneal injection. The mouse was first injected with 150 μg/kg-body weight pristane (sensitizer, purchased from Sigma-Aldrich Ltd.) for two weeks to reduce the mouse's immunity. Three days later from inoculation, the mouse was further fed with 20 Ci/kg-body weight of I-131, and 2 days later, a single photon emission computed tomography (SPECT) was used for the capability assessment of in vivo imaging to measure the amount of residual I-131 remaining within the mouse body and further determine the ability of the mutant-type NIS protein, NISQ218R, to absorb/transport I-131 within the mouse body. The result of the capability assessment of in vivo imaging is shown in FIG. 2 and Table 4.

TABLE 4

| NIS | NIS-wt | NIS-Q218R |
|---|---|---|
| Radioactive Strength | 0.267 ± 0.026 | 0.343 ± 0.012 |

Figure 2:
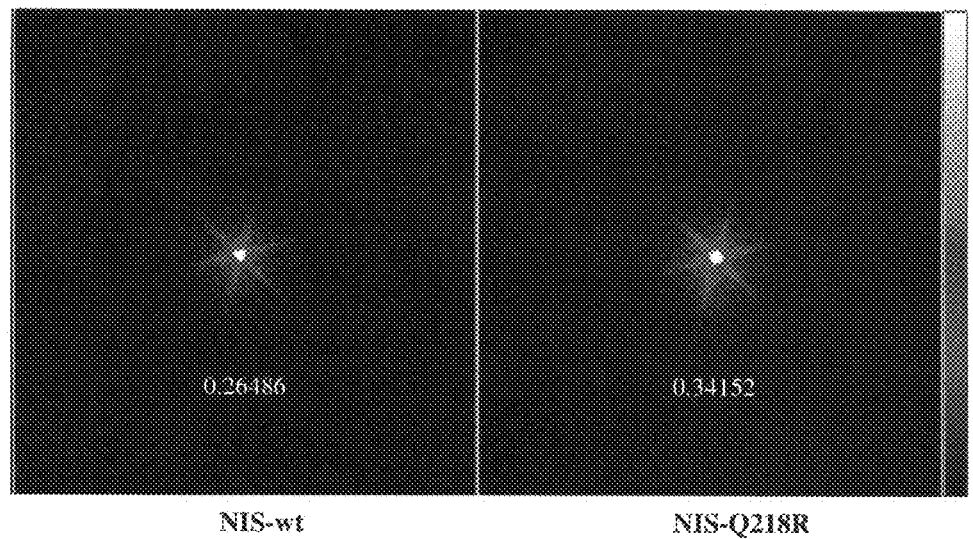
FIG. 2 is an in vivo molecular imaging picture showing I-131 within the mouse body.

From FIG. 2 and Table 4, it can be seen that compared to the mouse inoculated with the wild-type NIS protein, the radioactivity of I-131 was significantly higher in the mouse inoculated with the mutant-type NIS protein NIS-Q218R. The result illustrates that the NIS protein of the present invention can allow the cells to keep I-131 in the mouse body and increase the amount of radioactive iodine, and therefore, it can be used in cancer therapy or molecular imaging.

Example 5

Animal Test—Cytotoxicity Test

The mice inoculated with the mutant-type NIS protein, NIS-Q218R, or the wild-type NIS protein, NIS-wt, in Example 4 were fed for 9 days and then sacrificed. A phosphate buffered saline (PBS) solution was used to wash the abdominal cavity of the mice, and the abdominal rinsing liquid (containing tumor cells) was collected. A Cobra II auto-gamma counter was used to measure the radioactive intensity of I-131 in the abdominal rinsing liquid and to observe the effect of the mutant-type NIS protein NIS-Q218R enhancing the ability of I-131 to kill tumor cells. In the above process, I-131 that was not transported into tumor cells was excreted out of the mouse body, and thus, as the radioactivity lowered, it represents that the number of tumor cells reduced, and the NIS protein had a stronger ability to increase the ability of I-131 to kill tumor cells. The result is shown in Table 5.

TABLE 5

|  | Control group | NIS-wt | NIS-Q218R |
|---|---|---|---|
| Radioactivity* | 25.66 ± 4.04 | 6.4 ± 0.04 | 1.5 ± 0.71 |

*cpm, counts per minute/8.4 × $10^4$ cells

Table 5 shows that in the abdominal rinsing liquid of the mice inoculated with the mutant-type NIS protein NIS-Q218R, the radioactivity was obviously lower than that of the mice inoculated with the wild-type NIS protein, indicating that the NIS-Q218R protein has increased the cytotoxicity ability of I-131 to tumor cells. Thus, NIS-Q218R can increase the effect of I-131 to kill tumor cells by increasing the absorption of I-131 by tumor cells in the mouse body.

This example demonstrates that the NIS protein of the present invention can be applied to radioactive iodine therapy to increase the absorption ability of cancer cells to radioactive iodide ions to improve the cytotoxicity effect on cancer cells.

The above examples are provided to illustrate the principle and efficacy of the present invention, but not to limit the scope of protection thereof. People skilled in this field may proceed with a variety of modifications and replacements based on the above disclosures without departing from the principle and spirit of the present invention. Therefore, the scope of protection of the present invention is substantially covered in the following claims as appended.

What is claimed is:

1. A method for increasing a substrate of a sodium iodide symporter protein within a cell in vitro, comprising:
   a) introducing a modified sodium iodide symporter protein into a cell; and
   b) contacting the cell with one or more substrates of a sodium iodide symporter protein;
   wherein the modified sodium iodide symporter protein comprises the amino acid sequence of SEQ ID NO. 1 with the proviso that at least one of the following conditions is satisfied: (1) residue glutamine (Q) 218 is replaced by arginine (R); (2) residue threonine (T) 308 is replaced by lysine (K); and residue serine (S) 319 is replaced by aspartic acid (D); and expression of the modified protein in a cell results in higher intracellular levels of a substrate of a sodium iodide symporter protein than does expression of the same amount of a wild-type sodium iodide symporter protein; and the modified sodium iodide symporter protein is introduced into the cell by the following steps:
   a1) introducing an expression vector comprising a polynucleotide encoding the modified sodium iodide symporter protein into the cell; and
   a2) culturing the cell to express the modified sodium iodide symporter protein,
   wherein, the polynucleotide comprises a nucleic acid sequence of SEQ ID NO.2, SEQ ID NO.3, SEQ ID NO.4, SEQ ID NO.5, SEQ ID NO.6, SEQ ID NO.7, or SEQ ID NO.8.

2. The method as claimed in claim 1, wherein the polynucleotide comprises the nucleic acid sequence of SEQ ID NO.2.

3. The method as claimed in claim 1, wherein the substrate is sodium ion ($Na^+$), iodide ($I^-$), pertechnate ($TcO_4^-$), perrhenate ($ReO_4^-$), or astatide ($At^-$).

4. The method as claimed in claim 3, wherein the substrate is iodide ($I^-$).

5. The method as claimed in claim 1 for use in molecular imaging.

* * * * *

SEQUENCE LISTING

<160> NUMBER OF SEQ ID NOS: 17

<210> SEQ ID NO 1
<211> LENGTH: 643
<212> TYPE: PRT
<213> ORGANISM: homo sapiens

<400> SEQUENCE: 1

```
Met Glu Ala Val Glu Thr Gly Glu Arg Pro Thr Phe Gly Ala Trp Asp
1               5                   10                  15

Tyr Gly Val Phe Ala Leu Met Leu Leu Val Ser Thr Gly Ile Gly Leu
            20                  25                  30

Trp Val Gly Leu Ala Arg Gly Gly Gln Arg Ser Ala Glu Asp Phe Phe
        35                  40                  45

Ala Gly Gly Arg Arg Leu Ala Ala Leu Pro Val Gly Leu Ser Leu Ser
    50                  55                  60

Ala Ser Phe Met Ser Ala Val Gln Val Leu Gly Val Pro Ser Glu Ala
65                  70                  75                  80

Tyr Arg Tyr Gly Leu Lys Phe Leu Trp Met Cys Leu Gly Gln Leu Leu
                85                  90                  95

Asn Ser Val Leu Thr Ala Leu Leu Phe Met Pro Val Phe Tyr Arg Leu
            100                 105                 110

Gly Leu Thr Ser Thr Tyr Glu Tyr Leu Glu Met Arg Phe Ser Arg Ala
        115                 120                 125

Val Arg Leu Cys Gly Thr Leu Gln Tyr Ile Val Ala Thr Met Leu Tyr
    130                 135                 140

Thr Gly Ile Val Ile Tyr Ala Pro Ala Leu Ile Leu Asn Gln Val Thr
145                 150                 155                 160

Gly Leu Asp Ile Trp Ala Ser Phe Leu Ser Thr Gly Ile Ile Cys Thr
                165                 170                 175

Phe Tyr Thr Ala Val Gly Gly Met Lys Ala Val Val Trp Thr Asp Val
            180                 185                 190

Phe Gln Val Val Val Met Leu Ser Gly Phe Trp Val Val Leu Ala Arg
        195                 200                 205

Gly Val Met Leu Val Gly Gly Pro Arg Gln Val Leu Thr Leu Ala Gln
    210                 215                 220

Asn His Ser Arg Ile Asn Leu Met Asp Phe Asn Pro Asp Pro Arg Ser
225                 230                 235                 240
```

-continued

```
Arg Tyr Thr Phe Trp Thr Phe Val Val Gly Thr Leu Val Trp Leu
                245                 250                 255

Ser Met Tyr Gly Val Asn Gln Ala Gln Val Gln Arg Tyr Val Ala Cys
            260                 265                 270

Arg Thr Glu Lys Gln Ala Lys Leu Ala Leu Leu Ile Asn Gln Val Gly
            275                 280                 285

Leu Phe Leu Ile Val Ser Ser Ala Ala Cys Cys Gly Ile Val Met Phe
            290                 295                 300

Val Phe Tyr Thr Asp Cys Asp Pro Leu Leu Gly Arg Ile Ser Ala
305                 310                 315                 320

Pro Asp Gln Tyr Met Pro Leu Leu Val Leu Asp Ile Phe Glu Asp Leu
                325                 330                 335

Pro Gly Val Pro Gly Leu Phe Leu Ala Cys Ala Tyr Ser Gly Thr Leu
                340                 345                 350

Ser Thr Ala Ser Thr Ser Ile Asn Ala Met Ala Ala Val Thr Val Glu
                355                 360                 365

Asp Leu Ile Lys Pro Arg Leu Arg Ser Leu Ala Pro Arg Lys Leu Val
            370                 375                 380

Ile Ile Ser Lys Gly Leu Ser Leu Ile Tyr Gly Ser Ala Cys Leu Thr
385                 390                 395                 400

Val Ala Ala Leu Ser Ser Leu Leu Gly Gly Val Leu Gln Gly Ser
                405                 410                 415

Phe Thr Val Met Gly Val Ile Ser Gly Pro Leu Leu Gly Ala Phe Ile
                420                 425                 430

Leu Gly Met Phe Leu Pro Ala Cys Asn Thr Pro Gly Val Leu Ala Gly
            435                 440                 445

Leu Gly Ala Gly Leu Ala Leu Ser Leu Trp Val Ala Leu Gly Ala Thr
        450                 455                 460

Leu Tyr Pro Pro Ser Glu Gln Thr Met Arg Val Leu Pro Ser Ser Ala
465                 470                 475                 480

Ala Arg Cys Val Ala Leu Ser Val Asn Ala Ser Gly Leu Leu Asp Pro
                485                 490                 495

Ala Leu Leu Pro Ala Asn Asp Ser Ser Arg Ala Pro Ser Ser Gly Met
            500                 505                 510

Asp Ala Ser Arg Pro Ala Leu Ala Asp Ser Phe Tyr Ala Ile Ser Tyr
            515                 520                 525

Leu Tyr Tyr Gly Ala Leu Gly Thr Leu Thr Thr Val Leu Cys Gly Ala
            530                 535                 540

Leu Ile Ser Cys Leu Thr Gly Pro Thr Lys Arg Ser Thr Leu Ala Pro
545                 550                 555                 560

Gly Leu Leu Trp Trp Asp Leu Ala Arg Gln Thr Ala Ser Val Ala Pro
                565                 570                 575

Lys Glu Glu Val Ala Ile Leu Asp Asp Asn Leu Val Lys Gly Pro Glu
            580                 585                 590

Glu Leu Pro Thr Gly Asn Lys Lys Pro Pro Gly Phe Leu Pro Thr Asn
            595                 600                 605

Glu Asp Arg Leu Phe Phe Leu Gly Gln Lys Glu Leu Glu Gly Ala Gly
            610                 615                 620

Ser Trp Thr Pro Cys Val Gly His Asp Gly Gly Arg Asp Gln Gln Glu
625                 630                 635                 640

Thr Asn Leu
```

<210> SEQ ID NO 2
<211> LENGTH: 1932
<212> TYPE: DNA
<213> ORGANISM: artificial sequence
<220> FEATURE:
<223> OTHER INFORMATION: polynucleotide of mutant-type sodium iodide symporter protein

<400> SEQUENCE: 2

```
atggaggccg tggagaccgg ggaacggccc accttcggag cctgggacta cggggtcttt      60
gccctcatgc tcctggtgtc cactggcatc gggctgtggg tcgggctggc tcggggcggg     120
cagcgcagcg ctgaggactt cttcgccggg gccggcgcc tggcgcccct gcccgtgggc      180
ctgtcgctgt ctgccagctt catgtcggcc gtgcaggtgc tgggcgtgcc gtcggaggcc     240
tatcgctatg gctcaagtt cctctggatg tgcctgggcc agcttctgaa ctcggtcctc      300
accgccctgc tcttcatgcc cgtcttctac cgcctgggcc tcaccagcac ctacgagtac     360
ctggagatgc gcttcagccg cgcagtgcgg ctctgcggga ctttgcagta cattgtagcc     420
acgatgctgt acaccggcat cgtaatctac gcaccggccc tcatcctgaa ccaagtgacc     480
gggctggaca tctgggcgtc gttcctgtcc accggaatta tctgcaccttc tacacggct    540
gtgggcggca tgaaggctgt ggtctggact gatgtgttcc aggtcgtggt gatgctaagt     600
ggcttctggg ttgtcctggc acgcggtgtc atgcttgtgg gcgggcccg acgcgtgctc      660
acgctggccc agaaccactc ccggatcaac ctcatggact ttaaccctga cccgaggagc     720
cgctatacat tctggacttt tgtggtgggt ggcacgttgg tgtggctctc catgtatggc     780
gtgaaccagg cgcaggtgca cgctacgtg gcttgccgca cagagaagca ggccaagctg      840
gccctgctca tcaaccaggt cggcctgttc ctgatcgtgt ccagcgctgc tgctgtggc      900
atcgtcatgt ttgtgttcta cactgactgc gaccctctcc tcctggggcg catctctgcc     960
ccagaccagt acatgcctct gctggtgctg acatcttcg aagatctgcc tggagtcccc    1020
gggcttttcc tggcctgtgc ttacagtggc acccctcagca cagcatccac cagcatcaat    1080
gctatggctg cagtcactgt agaagacctc atcaaacctc ggctgcggag cctggcaccc    1140
aggaaactcg tgattatctc caaggggctc tcactcatct acggatcggc ctgtctcacc    1200
gtggcagccc tgtcctcact gctcggagga ggtgtcctcc agggctcctt caccgtcatg    1260
ggagtcatca gcggccccct gctgggagcc ttcatcttgg gaatgttcct gccggcctgc    1320
aacacaccgg cgtcctcgc gggactaggc gcgggcttgg cgctgtcgct gtgggtggcc     1380
ttgggcgcca cgctgtaccc acccagcgag cagaccatga gggtcctgcc atcgtcggct    1440
gcccgctgcg tggctctctc agtcaacgcc tctggcctcc tggacccggc tctcctccct    1500
gctaacgact ccagcagggc ccccagctca ggaatggacg ccagccgacc cgccttagct    1560
gacagcttct atgccatctc ctatctctat acggtgccc tgggcacgct gaccactgtg    1620
ctgtgcggag ccctcatcag ctgcctgaca ggcccccca agcgcagcac cctggccccg     1680
ggattgttgt ggtgggacct cgcacggcag acagcatcag tggcccccaa ggaagaagtg    1740
gccatcctgg atgacaactt ggtcaagggt cctgaagaac tccccactgg aaacaagaag    1800
ccccctggct cctgcccac caatgaggat cgtctgtttt cttggggca aaggagctg      1860
gagggggctg gctcttggac cccctgtgtt ggacatgatg gtggtcgaga ccagcaggag    1920
acaaacctct ga                                                        1932
```

<210> SEQ ID NO 3
<211> LENGTH: 1932
<212> TYPE: DNA
<213> ORGANISM: artificial sequence
<220> FEATURE:
<223> OTHER INFORMATION: polynucleotide of mutant-type sodium iodide
    symporter protein

<400> SEQUENCE: 3

| | | | | | | |
|---|---|---|---|---|---|---|
| atggaggccg | tggagaccgg | ggaacggccc | accttcggag | cctgggacta | cggggtcttt | 60 |
| gccctcatgc | tcctggtgtc | cactggcatc | gggctgtggg | tcgggctggc | tcgggcggg | 120 |
| cagcgcagcg | ctgaggactt | cttcgccggg | gccggcgcc | tggcgcccct | gcccgtgggc | 180 |
| ctgtcgctgt | ctgccagctt | catgtcggcc | gtgcaggtgc | tgggcgtgcc | gtcggaggcc | 240 |
| tatcgctatg | cctcaagtt | cctctggatg | tgcctgggcc | agcttctgaa | ctcggtcctc | 300 |
| accgccctgc | tcttcatgcc | cgtcttctac | cgcctgggcc | tcaccagcac | ctacgagtac | 360 |
| ctggagatgc | gcttcagccg | cgcagtgcgg | ctctgcggga | ctttgcagta | cattgtagcc | 420 |
| acgatgctgt | acaccggcat | cgtaatctac | gcaccggccc | tcatcctgaa | ccaagtgacc | 480 |
| gggctggaca | tctgggcgtc | gttcctgtcc | accggaatta | tctgcacctt | ctacacggct | 540 |
| gtgggcggca | tgaaggctgt | ggtctggact | gatgtgttcc | aggtcgtggt | gatgctaagt | 600 |
| ggcttctggg | ttgtcctggc | acgcggtgtc | atgcttgtgg | gcgggcccg | ccaggtgctc | 660 |
| acgctggccc | agaaccactc | ccggatcaac | ctcatggact | ttaaccctga | cccgaggagc | 720 |
| cgctatacat | tctggacttt | tgtggtgggt | ggcacgttgg | tgtggctctc | catgtatggc | 780 |
| gtgaaccagg | cgcaggtgca | gcgctacgtg | gcttgccgca | cagagaagca | ggccaagctg | 840 |
| gccctgctca | tcaaccaggt | cggcctgttc | ctgatcgtgt | ccagcgctgc | ctgctgtggc | 900 |
| atcgtcatgt | ttgtcttcta | caaggactgc | gaccctctcc | tcctgggcg | catctctgcc | 960 |
| ccagaccagt | acatgcctct | gctggtgctg | gacatcttcg | aagatctgcc | tggagtcccc | 1020 |
| gggcttttcc | tggcctgtgc | ttacagtggc | accctcagca | cagcatccac | cagcatcaat | 1080 |
| gctatggctg | cagtcactgt | agaagacctc | atcaaacctc | ggctgcggag | cctggcaccc | 1140 |
| aggaaactcg | tgattatctc | caaggggctc | tcactcatct | acggatcggc | ctgtctcacc | 1200 |
| gtggcagccc | tgtcctcact | gctcggagga | ggtgtccttc | agggctcctt | caccgtcatg | 1260 |
| ggagtcatca | gcggccccct | gctgggagcc | ttcatcttgg | aatgttcct | gccggcctgc | 1320 |
| aacacaccgg | cgtcctcgc | gggactaggc | gcgggcttgg | cgctgtcgct | gtgggtggcc | 1380 |
| ttgggcgcca | cgctgtaccc | acccagcgag | cagaccatga | gggtcctgcc | atcgtcggct | 1440 |
| gcccgctgcg | tggctctctc | agtcaacgcc | tctggcctcc | tggacccggc | tctcctccct | 1500 |
| gctaacgact | ccagcagggc | cccagctca | ggaatggacg | ccagccgacc | cgccttagct | 1560 |
| gacagcttct | atgccatctc | ctatctctat | tacggtgccc | tgggcacgct | gaccactgtg | 1620 |
| ctgtgcggag | ccctcatcag | ctgcctgaca | ggcccccca | agcgcagcac | cctggccccg | 1680 |
| ggattgttgt | ggtgggacct | cgcacggcag | acagcatcag | tggcccccaa | ggaagaagtg | 1740 |
| gccatcctgg | atgacaactt | ggtcaagggt | cctgaagaac | tccccactgg | aaacaagaag | 1800 |
| ccccctggct | tcctgcccac | caatgaggat | cgtctgtttt | tcttggggca | gaaggagctg | 1860 |
| gaggggctg | gctcttggac | cccctgtgtt | ggacatgatg | gtggtcgaga | ccagcaggag | 1920 |
| acaaacctct | ga | | | | | 1932 |

<210> SEQ ID NO 4
<211> LENGTH: 1932
<212> TYPE: DNA
<213> ORGANISM: artificial sequence
<220> FEATURE:
<223> OTHER INFORMATION: polynucleotide of mutant-type sodium iodide
    symporter protein

<400> SEQUENCE: 4

| | | |
|---|---|---|
| atggaggccg tggagaccgg ggaacggccc accttcggag cctgggacta cggggtcttt | 60 |
| gccctcatgc tcctggtgtc cactggcatc gggctgtggg tcgggctggc tcggggcggg | 120 |
| cagcgcagcg ctgaggactt cttcgccggg gccggcgcc tggcgccct gcccgtgggc | 180 |
| ctgtcgctgt ctgccagctt catgtcggcc gtgcaggtgc tgggcgtgcc gtcggaggcc | 240 |
| tatcgctatg gcctcaagtt cctctggatg tgcctgggcc agcttctgaa ctcggtcctc | 300 |
| accgccctgc tcttcatgcc cgtcttctac cgcctgggcc tcaccagcac ctacgagtac | 360 |
| ctggagatgc gcttcagccg cgcagtgcgg ctctgcggga ctttgcagta cattgtagcc | 420 |
| acgatgctgt acaccggcat cgtaatctac gcaccggccc tcatcctgaa ccaagtgacc | 480 |
| gggctggaca tctgggcgtc gttcctgtcc accggaatta tctgcaccctt ctacacggct | 540 |
| gtgggcggca tgaaggctgt ggtctggact gatgtgttcc aggtcgtggt gatgctaagt | 600 |
| ggcttctggg ttgtcctggc acgcggtgtc atgcttgtgg gcgggcccg ccaggtgctc | 660 |
| acgctggccc agaaccactc ccggatcaac ctcatggact ttaaccctga cccgaggagc | 720 |
| cgctatacat tctggacttt tgtggtgggt ggcacgttgg tgtggctctc catgtatggc | 780 |
| gtgaaccagg cgcaggtgca cgctacgtg gcttgccgca cagagaagca ggccaagctg | 840 |
| gccctgctca tcaaccaggt cggcctgttc ctgatcgtgt ccagcgctgc tgctgtggc | 900 |
| atcgtcatgt ttgtcttcta cactgactgc gaccctctcc tcctggggcg catcgatgcc | 960 |
| ccagaccagt acatgcctct gctggtgctg gacatcttcg aagatctgcc tggagtcccc | 1020 |
| ggcttttcc tggcctgtgc ttacagtggc acccctcagca cagcatccac cagcatcaat | 1080 |
| gctatggctg cagtcactgt agaagacctc atcaaacctc ggctgcggag cctggcaccc | 1140 |
| aggaaactcg tgattatctc caaggggctc tcactcatct acggatcggc ctgtctcacc | 1200 |
| gtggcagccc tgtcctcact gctcggagga ggtgtccttc agggctcctt caccgtcatg | 1260 |
| ggagtcatca gcggccccct gctgggagcc ttcatcttgg aatgttcct gccggcctgc | 1320 |
| aacacaccgg cgtcctcgc gggactaggc gcgggcttgg cgctgtcgct gtgggtggcc | 1380 |
| ttgggcgcca cgctgtaccc acccagcgag cagaccatga gggtcctgcc atcgtcggct | 1440 |
| gcccgctgcg tggctctctc agtcaacgcc tctggcctcc tggacccggc tctcctccct | 1500 |
| gctaacgact ccagcagggc ccccagctca ggaatggacg ccagccgacc cgccttagct | 1560 |
| gacagcttct atgccatctc ctatctctat acggtgccc tgggcacgct gaccactgtg | 1620 |
| ctgtgcggag ccctcatcag ctgcctgaca ggccccacca gcgcagcac cctggccccg | 1680 |
| ggattgttgt ggtgggacct cgcacggcag acagcatcag tggcccccaa ggaagaagtg | 1740 |
| gccatcctgg atgacaactt ggtcaagggt cctgaagaac tccccactgg aaacaagaag | 1800 |
| cccccctggct tcctgcccac caatgaggat cgtctgtttt tcttggggca gaaggagctg | 1860 |
| gagggggctg gctcttggac cccctgtgtt ggacatgatg gtggtcgaga ccagcaggag | 1920 |
| acaaacctct ga | 1932 |

<210> SEQ ID NO 5
<211> LENGTH: 1932
<212> TYPE: DNA
<213> ORGANISM: artificial sequence
<220> FEATURE:
<223> OTHER INFORMATION: polynucleotide of mutant-type sodium iodide
symporter protein

<400> SEQUENCE: 5

```
atggaggccg tggagaccgg ggaacggccc accttcggag cctgggacta cggggtcttt      60
gccctcatgc tcctggtgtc cactggcatc gggctgtggg tcgggctggc tcggggcggg     120
cagcgcagcg ctgaggactt cttcgccggg gccggcgcc tggcggccct gcccgtgggc      180
ctgtcgctgt ctgccagctt catgtcggcc gtgcaggtgc tgggcgtgcc gtcggaggcc     240
tatcgctatg gctcaagtt cctctggatg tgcctgggcc agcttctgaa ctcggtcctc      300
accgccctgc tcttcatgcc cgtcttctac cgcctgggcc tcaccagcac ctacgagtac     360
ctggagatgc gcttcagccg cgcagtgcgg ctctgcggga ctttgcagta cattgtagcc     420
acgatgctgt acaccggcat cgtaatctac gcaccggccc tcatcctgaa ccaagtgacc     480
gggctggaca tctgggcgtc gttcctgtcc accggaatta tctgcacctt ctacacggct     540
gtgggcggca tgaaggctgt ggtctggact gatgtgttcc aggtcgtggt gatgctaagt     600
ggcttctggg ttgtcctggc acgcggtgtc atgcttgtgg gcgggcccg acgcgtgctc      660
acgctggccc agaaccactc ccggatcaac ctcatggact ttaaccctga cccgaggagc     720
cgctatacat tctggacttt tgtggtgggt ggcacgttgg tgtggctctc catgtatggc     780
gtgaaccagg cgcaggtgca gcgctacgtg gcttgccgca cagagaagca ggccaagctg     840
gccctgctca tcaaccaggt cggcctgttc ctgatcgtgt ccagcgctgc tgctgtggc      900
atcgtcatgt ttgtcttcta caaggactgc gaccctctcc ctctggggcg catctctgcc     960
ccagaccagt acatgcctct gctggtgctg acatcttcg aagatctgcc tggagtcccc     1020
gggcttttcc tggcctgtgc ttacagtggc acccctcagca cagcatccac cagcatcaat    1080
gctatggctg cagtcactgt agaagacctc atcaaacctc ggctgcggag cctggcaccc    1140
aggaaaactcg tgattatctc caaggggctc tcactcatct acggatcggc ctgtctcacc    1200
gtggcagccc tgtcctcact gctcggagga ggtgtcctc agggctcctt caccgtcatg     1260
ggagtcatca gcggccccct gctgggagcc ttcatcttgg aatgttcct gccggcctgc    1320
aacacaccgg cgtcctcgc gggactaggc gcgggcttgg cgctgtcgct gtgggtggcc    1380
ttgggcgcca cgctgtaccc acccagcgag cagaccatga gggtcctgcc atcgtcggct    1440
gcccgctgcg tggctctctc agtcaacgcc tctggcctcc tggacccggc tctcctccct    1500
gctaacgact ccagcagggc ccccagctca ggaatggacg ccagccgacc cgccttagct    1560
gacagcttct atgccatctc ctatctctat acggtgccc tgggcacgct gaccactgtg    1620
ctgtgcggag ccctcatcag ctgcctgaca ggcccccaca gcgcagcac cctggccccg    1680
ggattgttgt ggtgggacct cgcacggcag acagcatcag tggcccccaa ggaagaagtg    1740
gccatcctgg atgacaactt ggtcaagggt cctgaagaac tccccactgg aaacaagaag    1800
ccccctggct tcctgcccac caatgaggat cgtctgtttt tcttggggca gaaggagctg    1860
gaggggctg gctcttggac cccctgtgtt ggacatgatg tgtggtcgaga ccagcaggag    1920
acaaacctct ga                                                        1932
```

<210> SEQ ID NO 6
<211> LENGTH: 1932
<212> TYPE: DNA
<213> ORGANISM: artificial sequence
<220> FEATURE:
<223> OTHER INFORMATION: polynucleotide of mutant-type sodium iodide symporter protein

<400> SEQUENCE: 6

| | | | | | |
|---|---|---|---|---|---|
| atggaggccg | tggagaccgg | ggaacggccc | accttcggag | cctgggacta | cggggtcttt | 60 |
| gccctcatgc | tcctggtgtc | cactggcatc | gggctgtggg | tcgggctggc | tcggggcggg | 120 |
| cagcgcagcg | ctgaggactt | cttcgccggg | gccggcgcc | tggcggccct | gcccgtgggc | 180 |
| ctgtcgctgt | ctgccagctt | catgtcggcc | gtgcaggtgc | tgggcgtgcc | gtcggaggcc | 240 |
| tatcgctatg | gctcaagtt | cctctggatg | tgcctgggcc | agcttctgaa | ctcggtcctc | 300 |
| accgccctgc | tcttcatgcc | cgtcttctac | cgcctgggcc | tcaccagcac | ctacgagtac | 360 |
| ctggagatgc | gcttcagccg | cgcagtgcgg | ctctgcggga | ctttgcagta | cattgtagcc | 420 |
| acgatgctgt | acaccggcat | cgtaatctac | gcaccggccc | tcatcctgaa | ccaagtgacc | 480 |
| gggctggaca | tctgggcgtc | gttcctgtcc | accggaatta | tctgcacctt | ctacacggct | 540 |
| gtgggcggca | tgaaggctgt | ggtctggact | gatgtgttcc | aggtcgtggt | gatgctaagt | 600 |
| ggcttctggg | ttgtcctggc | acgcggtgtc | atgcttgtgg | gcgggccccg | acgcgtgctc | 660 |
| acgctggccc | agaaccactc | ccggatcaac | ctcatggact | ttaaccctga | cccgaggagc | 720 |
| cgctatacat | tctggacttt | tgtggtgggt | ggcacgttgg | tgtggctctc | catgtatggc | 780 |
| gtgaaccagg | cgcaggtgca | gcgctacgtg | gcttgccgca | cagagaagca | ggccaagctg | 840 |
| gccctgctca | tcaaccaggt | cggcctgttc | ctgatcgtgt | ccagcgctgc | tgctgtggc | 900 |
| atcgtcatgt | ttgtgttcta | cactgactgc | gaccctctcc | cctggggcg | catcgatgcc | 960 |
| ccagaccagt | acatgcctct | gctggtgctg | acatcttcg | aagatctgcc | tggagtcccc | 1020 |
| gggcttttcc | tggcctgtgc | ttacagtggc | accctcagca | cagcatccac | cagcatcaat | 1080 |
| gctatggctg | cagtcactgt | agaagacctc | atcaaacctc | ggctgcggag | cctggcaccc | 1140 |
| aggaaactcg | tgattatctc | caaggggctc | tcactcatct | acggatcggc | ctgtctcacc | 1200 |
| gtggcagccc | tgtcctcact | gctcggagga | ggtgtcctc | agggctcctt | caccgtcatg | 1260 |
| ggagtcatca | gcggcccct | gctgggagcc | ttcatcttgg | aatgttcct | gccggcctgc | 1320 |
| aacacaccgg | cgtcctcgc | gggactaggc | gcgggcttgg | cgctgtcgct | gtgggtggcc | 1380 |
| ttgggcgcca | cgctgtaccc | acccagcgag | cagaccatga | gggtcctgcc | atcgtcggct | 1440 |
| gcccgctgcg | tggctctctc | agtcaacgcc | tctggcctcc | tggacccggc | tctcctccct | 1500 |
| gctaacgact | ccagcagggc | ccccagctca | ggaatggacg | ccagccgacc | cgccttagct | 1560 |
| gacagcttct | atgccatctc | ctatctctat | tacggtgccc | tgggcacgct | gaccactgtg | 1620 |
| ctgtgcggag | ccctcatcag | ctgcctgaca | ggcccacca | agcgcagcac | cctggccccg | 1680 |
| ggattgttgt | ggtgggacct | cgcacggcag | acagcatcag | tggcccccaa | ggaagaagtg | 1740 |
| gccatcctgg | atgacaactt | ggtcaagggt | cctgaagaac | tccccactgg | aaacaagaag | 1800 |
| cccccctggct | tcctgcccac | caatgaggat | cgtctgtttt | tcttggggca | gaaggagctg | 1860 |
| gaggggctg | gctcttggac | cccctgtgtt | ggacatgatg | gtggtcgaga | ccagcaggag | 1920 |
| acaaacctct | ga | | | | | 1932 |

<210> SEQ ID NO 7
<211> LENGTH: 1932
<212> TYPE: DNA
<213> ORGANISM: artificial sequence
<220> FEATURE:
<223> OTHER INFORMATION: polynucleotide of mutant-type sodium iodide symporter protein

<400> SEQUENCE: 7

```
atggaggccg tggagaccgg ggaacggccc accttcggag cctgggacta cggggtcttt      60
gccctcatgc tcctggtgtc cactggcatc gggctgtggg tcgggctggc tcggggcggg     120
cagcgcagcg ctgaggactt cttcgccggg gccggcgcc tggcggccct gcccgtgggc      180
ctgtcgctgt ctgccagctt catgtcggcc gtgcaggtgc tgggcgtgcc gtcggaggcc     240
tatcgctatg gctcaagtt cctctggatg tgcctgggcc agcttctgaa ctcggtcctc      300
accgccctgc tcttcatgcc cgtcttctac cgcctgggcc tcaccagcac ctacgagtac     360
ctggagatgc gcttcagccg cgcagtgcgg ctctgcggga ctttgcagta cattgtagcc     420
acgatgctgt acaccggcat cgtaatctac gcaccggccc tcatcctgaa ccaagtgacc     480
gggctggaca tctgggcgtc gttcctgtcc accggaatta tctgcacctt ctacacggct     540
gtgggcggca tgaaggctgt ggtctggact gatgtgttcc aggtcgtggt gatgctaagt     600
ggcttctggg ttgtcctggc acgcggtgtc atgcttgtgg gcgggcccg ccaggtgctc      660
acgctggccc agaaccactc ccggatcaac ctcatggact ttaaccctga cccgaggagc     720
cgctatacat tctggacttt tgtggtgggt ggcacgttgg tgtggctctc catgtatggc     780
gtgaaccagg cgcaggtgca cgctacgtg gcttgccgca cagagaagca ggccaagctg      840
gccctgctca tcaaccaggt cggcctgttc ctgatcgtgt ccagcgctgc tgctgtggc      900
atcgtcatgt ttgtcttcta caaggactgc gaccctctcc cctggggcg catcgatgcc     960
ccagaccagt acatgcctct gctggtgctg acatcttcg aagatctgcc tggagtcccc    1020
gggctttttcc tggcctgtgc ttacagtggc acccctcagca cagcatccac cagcatcaat    1080
gctatggctg cagtcactgt agaagacctc atcaaacctc ggctgcggag cctggcaccc    1140
aggaaactcg tgattatctc caagggctc tcactcatct acggatcggc ctgtctcacc    1200
gtggcagccc tgtcctcact gctcggagga ggtgtccttc agggctcctt caccgtcatg    1260
ggagtcatca gcggcccct gctgggagcc ttcatcttgg aatgttcct gccggcctgc    1320
aacacaccgg cgtcctcgc gggactaggc gcgggcttgg cgctgtcgct gtgggtggcc    1380
ttgggcgcca cgctgtaccc acccagcgag cagaccatga gggtcctgcc atcgtcggct    1440
gcccgctgcg tggctctctc agtcaacgcc tctggcctcc tggaccccgc tctcctccct    1500
gctaacgact ccagcagggc ccccagctca ggaatggacg ccagccgacc cgccttagct    1560
gacagcttct atgccatctc ctatctctat tacggtgccc tgggcacgct gaccactgtg    1620
ctgtgcggag ccctcatcag ctgcctgaca ggccccacca agcgcagcac cctggccccg    1680
ggattgttgt ggtgggacct cgcacggcag acagcatcag tggcccccaa ggaagaagtg    1740
gccatcctgg atgacaactt ggtcaagggt cctgaagaac tccccactgg aaacaagaag    1800
cccccctggct tcctgcccac caatgaggat cgtctgtttt cttggggca gaaggagctg    1860
gaggggggctg gctcttggac cccctgtgtt ggacatgatg gtggtcgaga ccagcaggag    1920
acaaaccttct ga                                                                1932
```

<210> SEQ ID NO 8
<211> LENGTH: 1932
<212> TYPE: DNA
<213> ORGANISM: artificial sequence
<220> FEATURE:
<223> OTHER INFORMATION: polynucleotide of mutant-type sodium iodide symporter protein

<400> SEQUENCE: 8

```
atggaggccg tggagaccgg ggaacggccc accttcggag cctgggacta cggggtcttt      60
gccctcatgc tcctggtgtc cactggcatc gggctgtggg tcgggctggc tcggggcggg     120
cagcgcagcg ctgaggactt cttcgccggg gccggcgcc tggcggccct gcccgtgggc      180
ctgtcgctgt ctgccagctt catgtcggcc gtgcaggtgc tgggcgtgcc gtcggaggcc     240
tatcgctatg gcctcaagtt cctctggatg tgcctgggcc agcttctgaa ctcggtcctc     300
accgccctgc tcttcatgcc cgtcttctac cgcctgggcc tcaccagcac ctacgagtac     360
ctggagatgc gcttcagccg cgcagtgcgg ctctgcggga ctttgcagta cattgtagcc     420
acgatgctgt acaccggcat cgtaatctac gcaccggccc tcatcctgaa ccaagtgacc     480
gggctggaca tctgggcgtc gttcctgtcc accggaatta tctgcacctt ctacacggct     540
gtgggcggca tgaaggctgt ggtctggact gatgtgttcc aggtcgtggt gatgctaagt     600
ggcttctggg ttgtcctggc acgcggtgtc atgcttgtgg gcgggcccg acgcgtgctc      660 acgctggccc agaaccactc ccggatcaac ctcatggact ttaaccctga cccgaggagc     720
cgctatacat tctggacttt tgtggtgggt ggcacgttgg tgtggctctc catgtatggc     780
gtgaaccagg cgcaggtgca cgctacgtg gcttgccgca cagagaagca ggccaagctg      840
gccctgctca tcaaccaggt cggcctgttc ctgatcgtgt ccagcgctgc tgctgtggc      900 atcgtcatgt ttgtcttcta caaggactgc gaccctctcc tcctggggcg catcgatgcc     960
ccagaccagt acatgcctct gctggtgctg acatcttcg aagatctgcc tggagtcccc     1020
gggcttttcc tggcctgtgc ttacagtggc accctcagca cagcatccac cagcatcaat     1080
gctatggctg cagtcactgt agaagacctc atcaaacctc ggctgcggag cctggcaccc     1140
aggaaactcg tgattatctc caaggggctc tcactcatct acggatcggc ctgtctcacc     1200
gtggcagccc tgtcctcact gctcggagga ggtgtccttc agggctcctt caccgtcatg     1260
ggagtcatca gcggcccct gctgggagcc ttcatcttgg aatgttcct gccggcctgc      1320 aacacaccgg cgtcctcgc gggactaggc gcgggcttgg cgctgtcgct gtgggtggcc     1380
ttgggcgcca cgctgtaccc acccagcgag cagaccatga gggtcctgcc atcgtcggct     1440
gcccgctgcg tggctctctc agtcaacgcc tctggcctcc tggacccggc tctcctccct     1500
gctaacgact ccagcagggc cccagctca ggaatggacg ccagccgacc cgccttagct      1560
gacagcttct atgccatctc ctatctctat tacggtgccc tgggcacgct gaccactgtg     1620
ctgtgcggag ccctcatcag ctgcctgaca ggccccacca gcgcagcac cctggccccg     1680 ggattgttgt ggtgggacct cgcacggcag acagcatcag tggcccccaa ggaagaagtg     1740
gccatcctgg atgacaactt ggtcagggt cctgaagaac tccccactgg aaacaagaag      1800
ccccctggct cctgcccac caatgaggat cgtctgtttt tcttggggca gaaggagctg     1860 gaggggctg gctcttggac ccctgtgtt ggacatgatg gtggtcgaga ccagcaggag      1920
acaaacctct ga                                                         1932
```

-continued

```
<210> SEQ ID NO 9
<211> LENGTH: 34
<212> TYPE: DNA
<213> ORGANISM: artificial sequence
<220> FEATURE:
<223> OTHER INFORMATION: primer

<400> SEQUENCE: 9
ccgtcggagg ccgatcgcta tggcctcaag ttcc                             34

<210> SEQ ID NO 10
<211> LENGTH: 32
<212> TYPE: DNA
<213> ORGANISM: artificial sequence
<220> FEATURE:
<223> OTHER INFORMATION: primer

<400> SEQUENCE: 10
gtcggaggcc cgccgctatg gcctcaagtt cc                               32

<210> SEQ ID NO 11
<211> LENGTH: 27
<212> TYPE: DNA
<213> ORGANISM: artificial sequence
<220> FEATURE:
<223> OTHER INFORMATION: primer

<400> SEQUENCE: 11
gggccccgac gcgtgctcac gctggcc                                     27

<210> SEQ ID NO 12
<211> LENGTH: 30
<212> TYPE: DNA
<213> ORGANISM: artificial sequence
<220> FEATURE:
<223> OTHER INFORMATION: primer

<400> SEQUENCE: 12
gtgctcaggc tagcccagaa ccactcccgg                                  30

<210> SEQ ID NO 13
<211> LENGTH: 27
<212> TYPE: DNA
<213> ORGANISM: artificial sequence
<220> FEATURE:
<223> OTHER INFORMATION: primer

<400> SEQUENCE: 13
gacccgaggc gccgctatac attctgg                                     27

<210> SEQ ID NO 14
<211> LENGTH: 34
<212> TYPE: DNA
<213> ORGANISM: artificial sequence
<220> FEATURE:
<223> OTHER INFORMATION: primer

<400> SEQUENCE: 14
gtcatgtttg tcttctacga tgactgcgac cctc                             34

<210> SEQ ID NO 15
<211> LENGTH: 34
<212> TYPE: DNA
<213> ORGANISM: artificial sequence
<220> FEATURE:
<223> OTHER INFORMATION: primer
```

```
<400> SEQUENCE: 15
gtcatgtttg tcttctacaa ggactgcgac cctc                          34

<210> SEQ ID NO 16
<211> LENGTH: 32
<212> TYPE: DNA
<213> ORGANISM: artificial sequence
<220> FEATURE:
<223> OTHER INFORMATION: primer

<400> SEQUENCE: 16
gcgaccctct tctcgatggg cgcatctctg cc                            32

<210> SEQ ID NO 17
<211> LENGTH: 30
<212> TYPE: DNA
<213> ORGANISM: artificial sequence
<220> FEATURE:
<223> OTHER INFORMATION: primer

<400> SEQUENCE: 17
ctggggcgca tcgatgcccc agaccagtac                               30
```